United States Patent [19]

Gilson

[11] 3,986,502

[45] Oct. 19, 1976

[54] AMBULATION ASSISTANCE DEVICE

[76] Inventor: Channing Wallace Gilson, 2046 Hillhurst Ave., Los Angeles, Calif. 90027

[22] Filed: June 16, 1975

[21] Appl. No.: 586,982

[52] U.S. Cl. ........................................ 128/83.5; 3/4; 135/68; 272/70.3

[51] Int. Cl.[2] ........................................ A61F 5/04

[58] Field of Search ............... 128/83.5, 83, 82, 80; 135/47.5, 49; 272/70.3, 70.4; 3/2, 4, 17

[56] References Cited

UNITED STATES PATENTS

| | | | |
|---|---|---|---|
| 267,680 | 11/1882 | Crandall | 135/49 |
| 1,277,009 | 8/1918 | Weldon | 135/49 |
| 1,323,629 | 12/1919 | Hall | 135/49 |
| 1,905,112 | 4/1933 | Lang | 3/4 |
| 1,934,346 | 11/1933 | Fisher | 128/83.5 |
| 2,762,367 | 9/1956 | Rubin | 128/83.5 |
| 3,254,659 | 6/1966 | Williams | 135/50 |
| 3,633,906 | 1/1972 | Fowler | 272/70.3 |

FOREIGN PATENTS OR APPLICATIONS

| | | | |
|---|---|---|---|
| 27,253 | 3/1905 | United Kingdom | 3/4 |

*Primary Examiner*—John D. Yasko
*Attorney, Agent, or Firm*—Donald D. Mon

[57] ABSTRACT

A device to assist ambulation. The device includes an arcuate edge whose center of curvature is located substantially at a point of load transfer from the body to the frame of the device. That point moves in the ambulation direction as a consequence of rolling contact of the arcuate edge with the ground. The arc is not necessarily a circular arc. In one embodiment, the load transfer point is at the knee, and the device can increase the stride of a normal leg or can act as a prosthetic substitution for a missing lower part of a leg. In another embodiment, the load transfer point can be at the armpit, and the device becomes a support in the nature of a crutch that renders crippled ambulation surprisingly smooth and stable. In fact, the device is so stable that the user can at least partially be sling-supported by it. In another embodiment, the load transfer point is at the hand, and the device can be used as a cane.

30 Claims, 15 Drawing Figures

FIG. 1
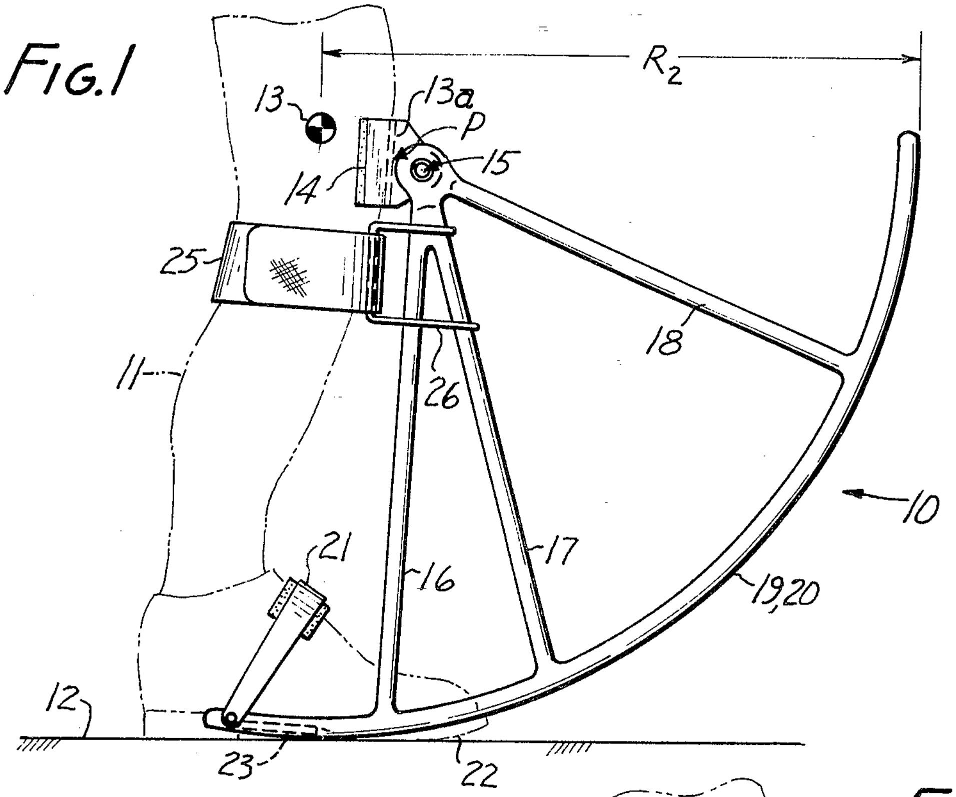
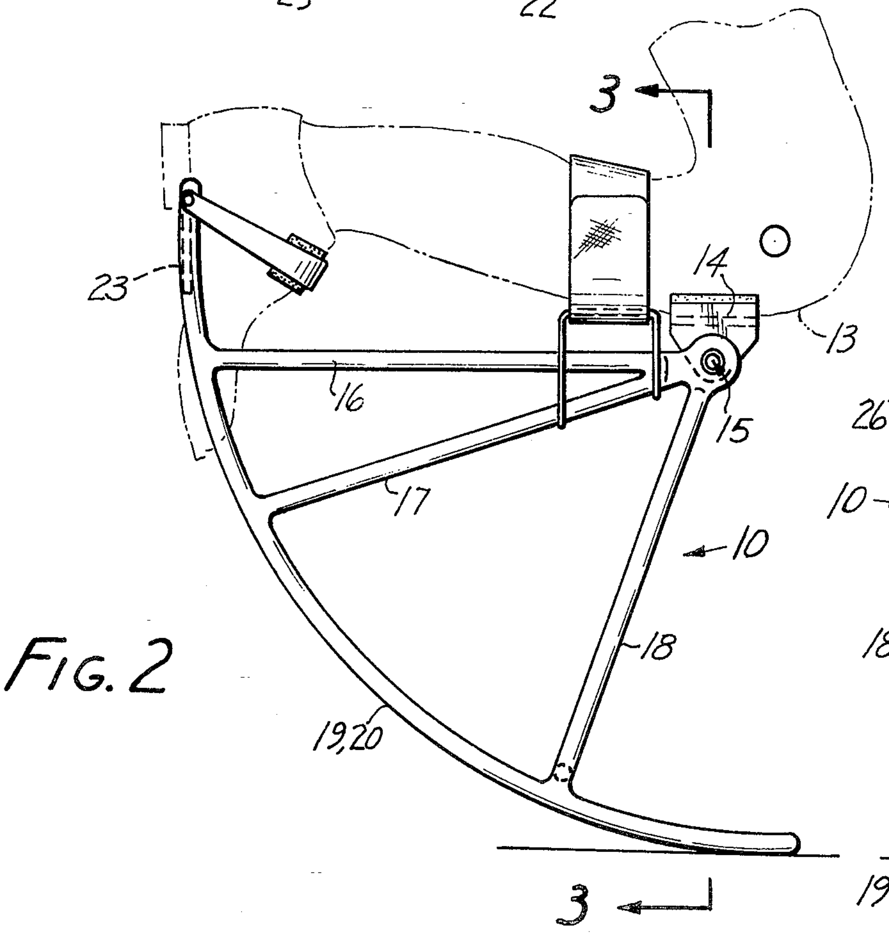
FIG. 2
FIG. 3
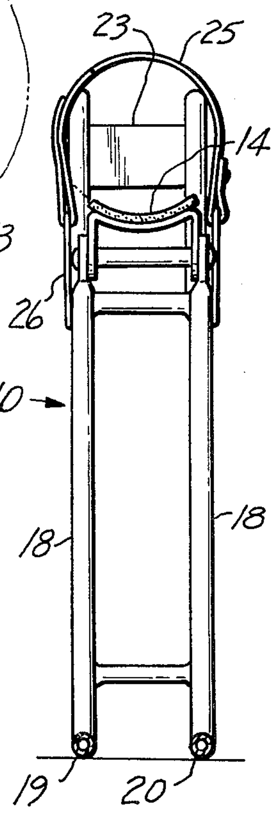

FIG.10
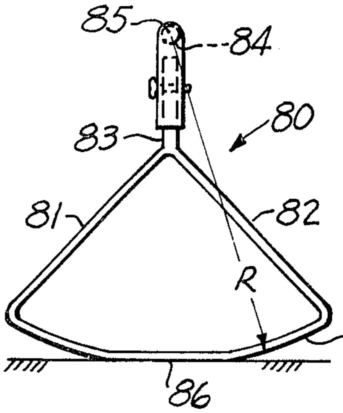
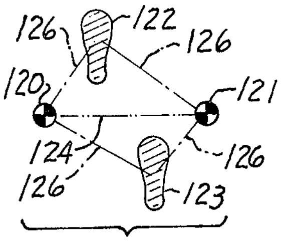
FIG.9
FIG.4
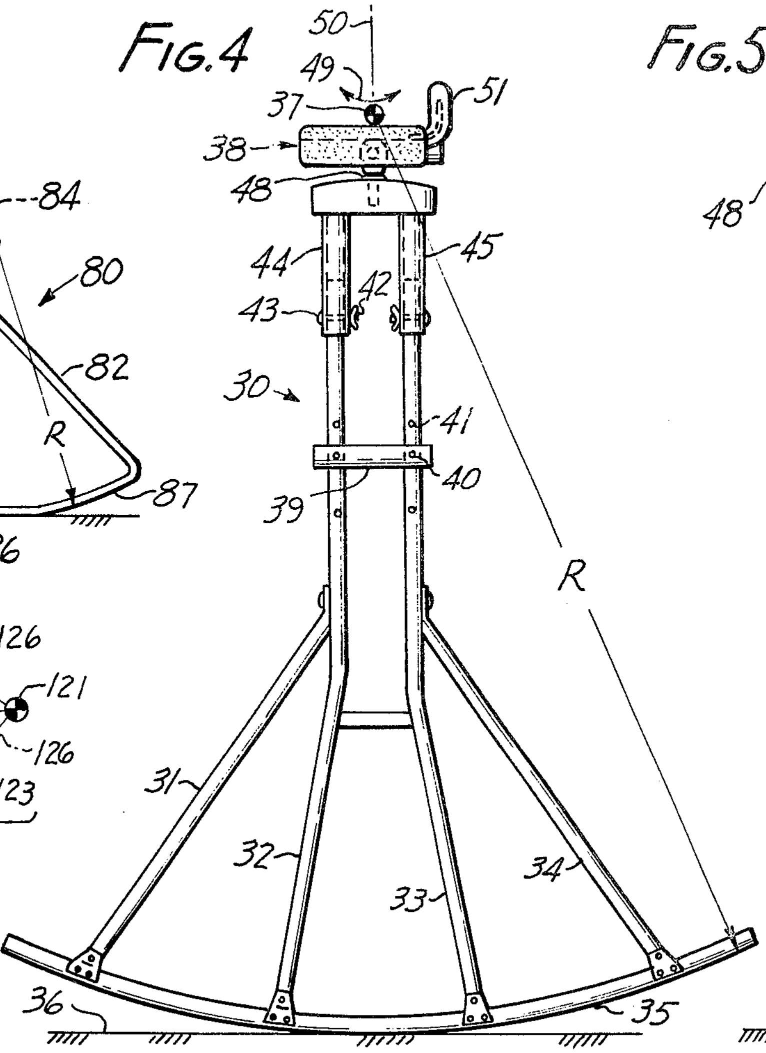
FIG.5
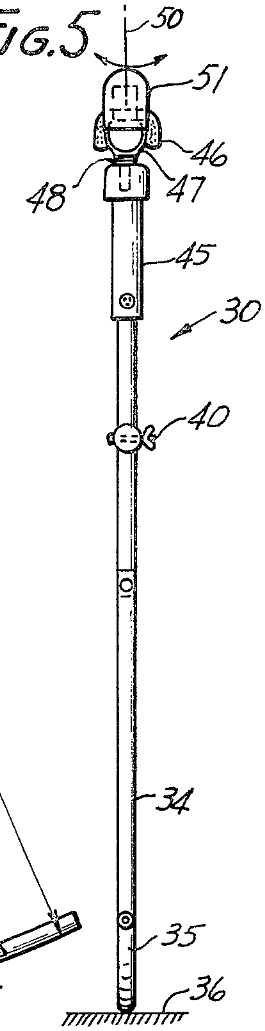
FIG.6
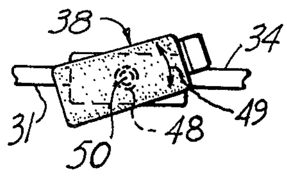
FIG.7
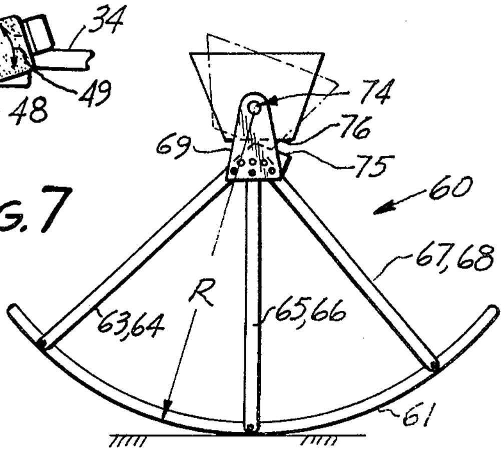
FIG.8
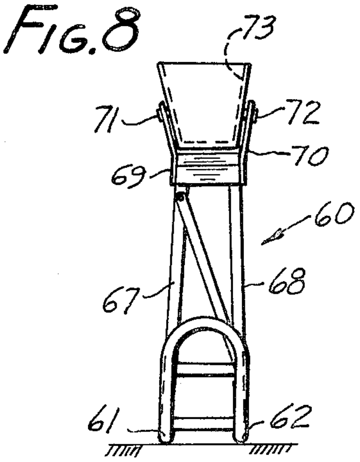

AMBULATION ASSISTANCE DEVICE

This invention relates to an ambulation assistance device.

Ambulation is customarily limited by the length of the individual's stride. The length of the stride varies with the individual's height and with the distance by which he can move one foot ahead of the other.

It is an object of this invention to provide and ambulation assistance device which increases the stride length without requiring an increase in the forward arcuate movement of the legs.

Further, it is known that persons who are missing portions of their legs from the hip down, and especially at the knee, frequently require inconvenient prosthetic devices, such as peg-legs, which limit the length of their stride. It is another object of this invention to provide a prosthetic means which can be utilized by persons missing portions of their legs, which will increase their stride.

Persons who have required the use of crutches following illness or breakage of legs are aware of the difficulties inherent in the use of conventional crutches. These include the shock imposed in the armpits at each step, the need to swing up over the top of an arc centered where the crutch point contacts the ground, and the need to swing the body in a relatively uncontrolled arc from the top of the crutch up and over a vertical centerline.

It is another object of this invention to provide an ambulation device in the nature of a crutch which supports the body at the armpit at a substantially constant elevation and without imposing shock loads on the body each time the crutch is advanced ahead of the body. In fact, the device can even support a sling or seat at least partially to support the user.

It is still another object of this invention to provide a device of this type which can be used as an improved cane.

An ambulation assistance device according to this invention includes a body having an arcuate edge whose center of curvature is located substantially at a point of load transfer from the body to the frame of the device. The arcuate edge need not be circularly arcuate, although it usually will be. This point of load transfer therefore moves along at a substantially constant elevation, and the length of the stride of the user is elongated by the arcuate edge which rolls along the ground ahead of the toe.

In one embodiment of the invention, the load transfer point is the knee, and means is provided for attaching the foot of the user to the device adjacent to the arcuate edge, whereby his foot takes its normal stride. After the load is transferred to the knee, the stride is lengthened by the amount of arcuate edge ahead of the toe.

According to another embodiment of the invention, the point of load transfer is the armpit. Preferably, a load-bearing pad on which the user bears is pivotal around the central axis of the device itself.

According to yet another embodiment of the invention, a sling or seat can be pivotally mounted to the frame at least partially to support the user.

According to still another preferred but optional feature of the invention, means is provided for supporting the terminal end of an imcomplete limb to transfer the load.

According to yet another preferred but optional feature of the invention, the device may be adapted for use as a cane.

The above and other features of this invention will be fully understood from the following detailed description and the accompanying drawings, in which:

FIG. 1 is a side elevation of one embodiment of the invention in a first operating position;

FIG. 2 shows the device of FIG. 1 in a second operating position;

FIG. 3 is a right-hand view taken at line 3—3 of FIG. 2;

FIGS. 4, 5 and 6 are respectively a side, end, and top view of another embodiment of the invention;

FIGS. 7 and 8 are respectively side and end elevations of another embodiment of the invention;

FIG. 9 is a schematic view illustrating the inherent stability of the device of FIGS. 4–6;

FIG. 10 is a side view of the invention useful as a cane;

Figure 11:
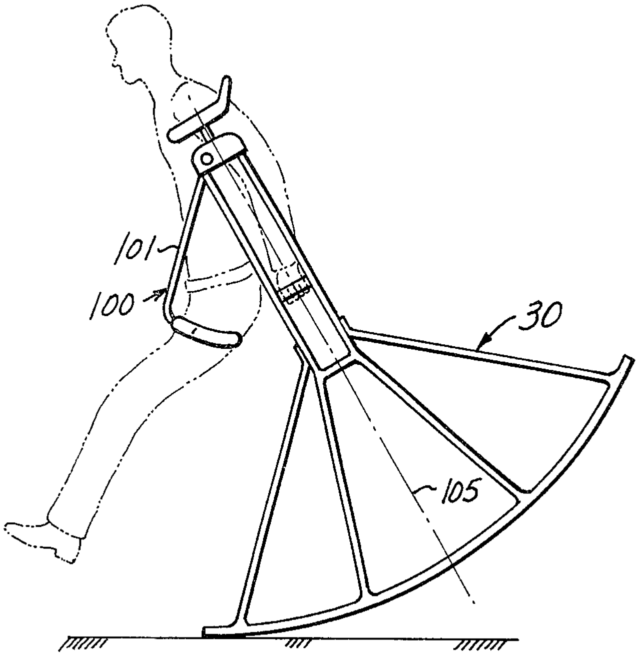
FIGS. 11 and 12 are sequential side views showing the device of FIGS. 4–6 modified to provide additional means to support the user.
Figure 12:
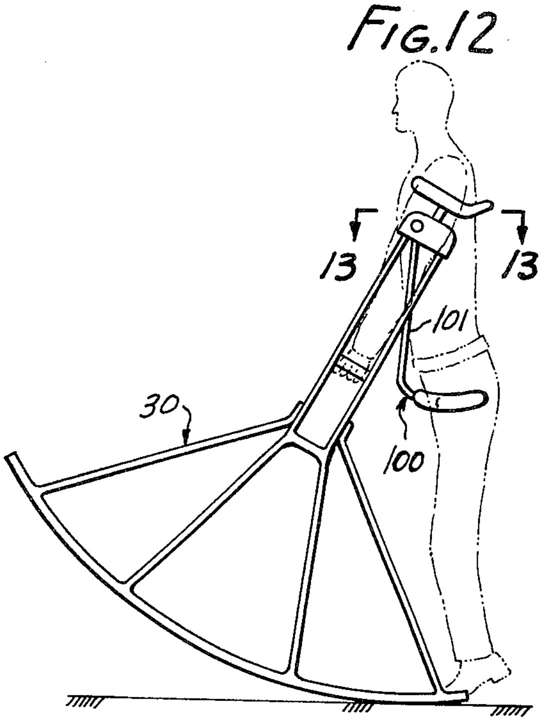
Figure 13:
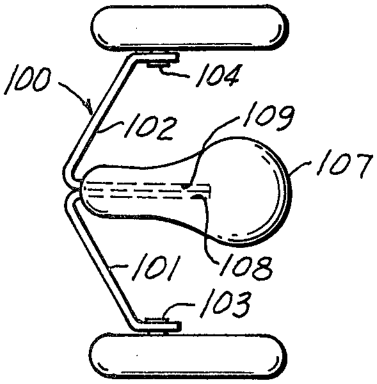
FIG. 13 is a modified top view of FIG. 12 taken at line 13—13 therein.
Figure 14:
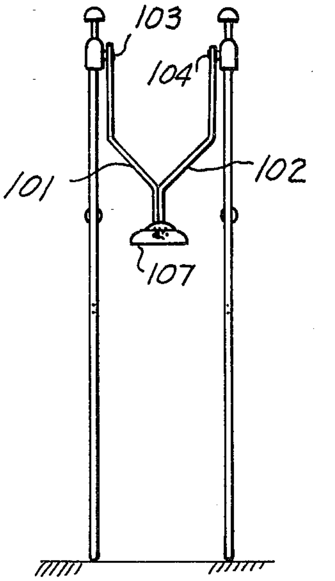
FIG. 14 is a side view of FIG. 13.

One embodiment of the invention is shown in FIG. 1 wherein an ambulation assistance device 10 is shown strapped to the lower leg 11 of a user. The user's foot is shown standing on the ground 12. The hinge point 13 of the user's knee 13*a* is the point of load transfer for this individual. Of course, the direct contact is at a knee pad 14, but the structural members, i.e., the bones, tend to act through point 13, and for convenience this will be regarded as the "point of load transfer". For convenience, the knee pad is hinged at hinge 15. The frame device includes struts 16, 17, 18 which extend in pairs to arcuate edges 19, 20. If desired, the struts can be made telescopic so their length can be adjusted. The arcuate edges preferably (although not necessarily) are circularly arcuate at their outermost surface which contacts the ground of radius R. Their curvature should be identical so they give lateral support. The load transfer point need not be precisely at the center of curature of the arcuate edges, but the closer to the center the more effective the device will be.

The foot is held to the device by an adjustable strap 21 which is attached to both of the arcuate edges, and which presses the sole 22 of the shoe against a plate 23 which extends across the spacing between the two arcuate edges. Therefore, the shoe is strapped to the arcuate edges. This arrangement still allows the ball of the foot to make contact with the ground during at least part of the stride and gives freedom of the toes to move for better balance control. A knee strap 25 is attached to hooks 26 on opposite sides of the struts so that the strap can be wrapped around the knee to hold the knee against the knee pad. Fastener means, such as hooks or Velcro pads, are provided on the knee strap for attachment purposes. The strap is ideally elastic, thereby providing adaptation for flexure of the calf muscle as the leg moves.

The device of FIGS. 1—3 is utilized primarily to increase the length of the user's stride. It can be used as a means to increase the distance a person can walk in a given time with a given number of steps for useful purposes or merely for entertainment. It can, for example, be used by children in playing games or merely in idly amusing themselves. Balancing poles, such as ski poles, can be used by beginners to stabilize themselves.

The device of FIGS. 4, 5 and 6 is for use as a crutch. It constitutes an ambulatory assistance device 30 wherein a plurality of struts 31, 32, 33, 34 are joined to one another and also to an arcuate edge 35 which makes contact with the surface of the ground 36. The arcuate edge is preferably circular, although it is not necessarily circular. As will later be disclosed, the curvature may vary. In any event, the point of load transfer should be adjacent to the center of curvature (as later described). When the arc is circular, the center 37 of curvature of the arc of radius R is substantially at the point of load transfer which, in this case, is at a load transfer means comprising rail means 38 mounted to the top of the crutch, and adapted to enter the armpit.

In accordance with common crutch construction, a handhold 39 is provided along the two vertical struts 32 and 33, so it may adjustably be moved up and down to accommodate different arm lengths, and can be held in the adjusted position by pins 40 in aligned holes 41 in the struts. Similarly, the upper portion of the crutch may be made adjustable by providing fastener means, such as wing nuts 42 and bolts 43, to hold a pair of telescopic joings 44, 45 in an adjusted position. This may move the point of load transfer somewhat from the center of curvature, but if the device is inventoried in several basic curvatures, then reasonable adjustments may be made to accommodate individual heights without excessive deterioration of the advantages of this device by establishing the point of load transfer too far from the actual center of curvature. The crutch can be provided in any number of curvatures, but too many sizes would require too much inventory.

Rail means 38 includes shock absorbing means 46 comprising a layer of resilient and compressible material such as sponge rubber incorporated in this load transfer means by being laid over a hard substructure 47. The term "rail means" connotes a relatively thin, elongated member which can conveniently be fitted in the armpit without excessively holding the arm out to the side. A pivot joint 48 enables the rail means to be rotated bidirectionally, as shown by arrows 49 (FIG. 6), around the central axis 50 of the device. This provides important advantages which will later be discussed. A retention tab 51 is provided at the rear of rail means 38.

FIGS. 7 and 8 show the device of FIG. 1 adapted for use by a person who is missing part of his lower leg. In these FIGS., ambulation assistance device 60 includes arcuate edges 61, 62 and struts 63, 64, 65, 66, 67, 68 attached to the edges and to plates 69, 70 to which hinge pins 71, 72 are attached. A receptacle 73 is hinged to the pins, and point 74 of load transfer is substantially where the person's knee pivot point would be had he still had his entire leg. Means, not shown, may be provided for strapping the device so as to retain the knee therein. Particular attention is shown to stop surfaces 75 and **75*a* attached to the struts, and 76 and 76*a* on the receptacle. These limit the forward and backward tilt of the receptacle. The forward limitation is shown in dashed line in FIG. 7,** and the rearward limit is angularly opposite. A rotary force can be exerted on the device when the wearer leans forwardly or backwardly. Also, the system is prevented from "buckling" at that point. It will be understood that the receptacle shown is only one type of adaptation. Should the person be missing portions of his leg above the knee, the radius R could be made larger, and strap means or other devices could be provided to attach the device to the user.

FIG. 10 shows an ambulation assistance device 80 useful as a cane. It includes a pair of struts 81, 82 and an upright rod 83 joined to them with a handle 84 telescopically coupled to it. The handle is preferably located at the center of curvature 85 of the arcuate radius R. This device may either be single-tracked as the crutch of FIG. 4, or double-tracked as in the device of FIG. 7. Customarily, it will be double-tracked for additional stability. Also for additional stability, a flat region 86 may be provided on the bottom of the arcuate edges so as to tend to center the device. This flat region need not be of major length, but may be if desired. In any event, it will enable the user to enjoy additional stability of the device in its centermost position. A centering flat region can also be provided on the arcuate edges of the other embodiments of the invention, but would be less desirable in the other embodiments, because of the shock transmitted to the knee or the armpit when the edge rolls over the flat region.

FIGS. 11–14 show a modification of the device of FIGS. 4–6. The general structure 30 is all present. What is added is support means 100 by way of a sling or swing upon which the user can rest as he swings forward. The support means includes a pair of suspension members 101, 102, that are pivotally mounted to the upper portion of the frame of the crutch at the point of load transfer to the frame. The pivots 103, 104 should be disposed somewhat forwardly of the centerline 105 of the crutch, because this gives a forward torque toward the end of the movement. However, they can instead be placed on the centerline, if preferred.

A seat member 107 has a pair of sockets 108, 109 to receive end prongs of the suspension members. The seat, shaped rather like a bicycle seat, is straddled by the user, and the suspension members are shaped so as to clear the body. The seat is preferably a little closer to the ground than the crotch of the user when standing so the crutch can be lifted from the ground by a standing movement to advance it.

Figure 15:
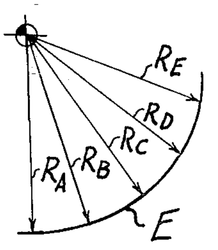
FIG. 15 shows another embodiment of arcuate edge.

FIG. 15 illustrates that the arcuate edge ("E" in FIG. 15) need not be circular. Instead a spiral shape or other arc with a changing radius can be used. The center of curvature is, in this case, the center of each individual short segment of arc, and a plurality of radii $R_A$, $R_B$, $R_C$, $R_D$, etc. are shown, which are of progressively decreasing length. The result is a tendency for accelerated motion toward the end of a step.

Throughout this specification, the rigid structure to which the arcuate edge or edges is attached is called the "frame", and the center of curvature is adjacent to the point of load transfer to the frame. When the device is used as a cane, crutch, or attachment to the foot, knee or leg, the body weight is directly transmitted to the frame. In the device of FIGS. 11–14, however, the body weight is taken directed or in part by the support and is transferred by the support to the frame to the point of load transfer. This illustrates that the embodiments of this invention can be utilized not only to receive the body weight directly, but also indirectly through other supporting means. All of the embodiments have in common, however, that the weight is actually applied to the frame at a point of load transfer substantially adjacent to the center of curvature.

The use and operation of the devices will now be described. In FIG. 1 the device is strapped to the leg, and in the first position the user simply stands up as shown. Before the device comes into use, he will have swung his foot forwardly for the first half of his normal stride, striking the ground with his heel, and advancing to the position of FIG. 1. With additional forward movement, the ground contact changes from the foot to the arcuate edge, and the point of load transfer shifts from the foot to the knee. If the hinge point 13 is at the center of curvature of the arcuate edge, it will not change elevation as the stride advances. However, with any practical device, there will be a small change in eievation, but this will not usually be bothersome. By providing adjustment means, even this small increment can be decreased or eliminated. However this may be, the point of load transfer moves forward in the direction of ambulation, and the foot leaves the ground. The contact point of the arcuate edge with the ground will advance in the forward direction of ambulatory motion, and this motion will continue until the knee is directly over the end of the arcuate edge as shown in FIG. 2. It will be observed that the length of this one stride has been increased over that which would be attained in normal stride by the amount by which the length of the arcuate edge exceeds that portion of the stride which the user can provide to it. Suffice it to say that this device provides a substantial increase in the length of stride when moved to its maximum. At this point in the stride, or perhaps somewhat ahead of it, the other leg will be swung forwardly to repeat the action on the other side.

In the device of FIGS. 1—3 it is useful to provide two arcuate edges on each device in order to give two points of contact which are laterally spaced apart relative to the axis of forward motion. However, it is not necessary that there be two individual arcuate edges. Instead, the region may be filled in with a tread much like an automobile tire, and can even be reduced to one narrow arcuate edge like an ice skate, if desired. However, the construction shown is both useful and safe.

The arcuate edges can be made of tubular members as shown which are relatively easy to bend to the desired arcuate shape, or they may be more rigid members cut or bent to shape. The struts may be welded or attached by screws or fasteners thereto. Skid-resistant material (not shown) may be attached to the bottom of the arcuate edges, or the arcuate edges themselves may be roughened or otherwise treated to resist skidding. In this and all the other embodiments, the struts are shown together with independent arcuate edges, because this represents a very lightweight type of construction. However, solid bodies without cutouts may be provided, and more or fewer struts may be provided with appropriate adjustment of their strength.

The device of FIGS. 4–6 operates much the same as a common crutch, but with a very substantial improvement in performance. It will be noted that if the point of load transfer is substantially at the center of curvature of the arcuate edges, the user can move along as though his armpits were resting upon the axle of a wheel with the same radius. Accordingly, all the user need do is simply move the device forward around the center of curvature and move along relative to it, either assisting himself by walking or by swinging himself with or without the support means of FIGS. 11–14. In each case it does not require that the user raise or lower the elevation of his armpits at each step as with a common crutch. Neither does it require that he swing the crutch in a sideward and outward arc to get it around to a forward position as in a common crutch.

The pivoting motion of the rail means 38 around the vertical axis compensates for the movement which occurs in the human body such that when the shoulder is moved forward and backward, there is rotation at the armpit. In common crutches, the crutch is rotated because the pad is trapped and rotates. The pivoting pad arrangement enables the left and right devices to be held parallel to each other at all times, and parallel to the line of forward motion without the device's cocking, which almost unconsciously occurs when a common crutch bearing on the ground at one point is used. The forward motion can therefore be very smooth and easy on the user.

Furthermore, the crutch shown in FIGS. 4–6 is very stable. The weight transferred to the ground is by a vertical force at the point of contact, and these are always side by side (see FIG. 9) where contact points 120, 121 are shown. The feet 122, 123 are at most times on opposite sides of a line 124 drawn between points 120 and 121. As a result, a parallelogram pattern (line 126) is developed which is a stable base. This is very different from standard crutches where both feet are usually either ahead of or behind the contact points. When the user goes off balance, either forward or backward, this device, because of its constant ground-to-shoulder distance feature, brings the user to rest in a stable position, which might even be straight up with both feet on line 124. By contrast, when a user of ordinary crutches goes off balance fore or aft, the user falls to the ground.

When the body swings forward, suspended from the armpit beneath the shoulder joint, the shoulder joint moves back and the arm follows. When the body swings backward, the reverse motions occur, and the shoulder travel back and forth is not linear, but pivotal motion about the central body axis, forcing any crutch pad in the armpit also to pivot around the rib cage and around the central body axis.

In FIGS. 7 and 8, the device functions like the device of FIGS. 1—3 with the exception that, because the user has no foot, there are no means to strap the foot near the arcuate edge. Instead, the knee or whatever part of the lower extremity is used is attached to the receptacle, and when the user swings the device forward on his forward stride, the device swings forward of that shown in FIG. 6, and then he moves forwardly relative to it until finally the stop surfaces engage one another, and the user's forward momentum continues the forward motion as shown.

In the device of FIG. 10, especially when the flat region 86 is provided on the arcuate edges, the device is free-standing and will remain erect. This region provides a point of reference for the user. As he walks along, the point of load transfer, i.e., the hand-hold, remains vertically above the point of contact with the ground, and the user has a point of reference straight down. Except for the minor transitional effects adjacent to the flat region, there is no tendency of the device to move forwardly or backwardly to any particular position, and the user therefore can lean straight down on the handle, and it will remain just as still as though it where a wheel, without any tendency for forward or rearward direction. When there are two parallel arcuate edges, then there is also resistance to lateral tipping over. The device may be used as an ordinary cane, being swung forward and held in place on the ground as the user moves forward relative to it. Again, it is emphasized that the point of load transfer is substantially adjacent to the center of curvature, and the user may move along relative to that point almost as though his arm was mounted to a wheel whose hub is his shoulder. There is surprising stability and amplification of stride.

This invention thereby provides ambulation assistance means which provide the user with considerable stability, both for crippled or handicapped persons and for persons who merely wish to lengthen the distance of each stride.

When it is said that the center of curvature is substantially adjacent to the load transfer point, it is meant that these are not so far apart as unacceptably to degrade the performance of the device. The term "adjacency" includes contiguity and also includes coincidence of the points. A vertical spacing apart of perhaps an inch or two is usually acceptable, but much more than that can cause excessive raising and lowering of the body. When a non-circular arc is used, the spacing apart primarily relates to spacing along a line connecting them and including the point of contact with the ground, because the immediate radius is that of a small segment of the arcuate edge.

The term "load transfer means" defines the means whereby the frame receives the weight. In FIG. 1, it is the knee pad and straps. In FIG. 4, it is the pad. In FIG. 10, it is the handle. In FIGS. 11–14, it is the pivotal point at which the supports are attached. It follows that the load transfer means is not necessarily congruent with the point at which the body is actually supported by the entire device, but instead relates to the point at which the load is transferred to the frame itself.

The length of the arc will be appropriate to the radius of curvature. In FIG. 1, it will usually approach the length respective to 90° (including the length of the foot), and in FIGS. 10 and 11 usually somewhat less than 180°, perhaps about 140°. This is so the point of load transfer will be over the point of contact (or at least not deleteriously forward of it) at all times, i.e., the user should not be able to fall forwardly over the tip of the arcuate edge in routine usage.

Shock absorbing means similar to layer 46 can be incorporated in the embodiment of FIG. 1 between knee pad 14, and in FIG. 7 in the bottom of the receptacle. The purpose, wherever used, is to cushion the shock of load transfer.

If desired, limited arcuate motion of the foot relative to the frame can be permitted in the device of FIG. 1 by pivoting the plate against which the sole bears. Flexure at the angle reduces the risk of muscular cramping.

This invention is not to be limited by the embodiments shown in the drawings and described in the description, which are given by way of example and not of limitation, but only in accordance with the scope of the appended claims.

I claim:

1. An ambulation assistance device comprising: a frame including an arcuate edge for contacting the ground, said arcuate edge having a center of curvature; load transfer means on said frame engageable to or by the body for transferring body weight to the frame, and so disposed and arranged that the point of load transfer in the kinetics of the body is disposed substantially adjacent to the said center of curvature; and means adjacent to the arcuate edge for attachment to the foot of the user, whereby the foot makes contact with the ground during at least part of its stride.

2. A device according to claim 1 in which the arcuate edge is circularly arcuate.

3. A device according to claim 1 in which the radius of curvature of the arcuate edge decreases in the forward direction.

4. A device according to claim 1 in which a flat region is formed on the arcuate edge which is recessed from the path of the arcuate edge.

5. A device according to claim 1 in which a strap is provided to hold the knee against the load transfer means.

6. A device according to claim 1 in which the arcuate edge is formed by two laterally spaced-apart curved members.

7. A device according to claim 6 in which a strap is provided to hold the knee against the load transfer means.

8. A device according to claim 7 in which means is provided between the curved members for attachment of the foot of a user.

9. A device according to claim 1 in which the means for attachment of the foot permits pivotal movement at the ankle joint without arcuately moving the frame.

10. An ambulation assistance device comprising: a frame including an arcuate edge for contacting the ground, said arcuate edge having a center of curvature; load transfer means on said frame engageable to or by the body for transferring body weight to the frame, and so disposed and arranged that the point of load transfer in the kinetics of the body is disposed substantially adjacent to the said center of curvature; and a leg-receiving receptacle pivotally mounted to the frame, the point of pivotal mounting of the receptacle being substantially coincident with the load transfer point.

11. A device according to claim 10 in which stop surfaces are carried by the frame and by the receptacle to limit the pivoting movement of the receptacle in both the forward and reverse directions.

12. A device according to claim 10 in which the receptacle is ring-like to receive the stump of a leg.

13. A device according to claim 12 in which stop surfaces are carried by the frame and by the receptacle to limit the pivoting movement of the receptacle in both the forward and reverse directions.

14. A device according to claim 10 in which the receptacle is an open-topped container to receive the stump of a leg.

15. A device according to claim 14 in which stop surfaces are carried by the frame and by the receptacle to limit the pivoting movement of the receptacle in both the forward and reverse directions.

16. A device according to claim 10 in which the arcuate edge is formed by two laterally spaced-apart curved members.

17. An ambulation assistance device comprising: a frame including an arcuate edge for contacting the ground, said arcuate edge having a center of curvature; load transfer means on said frame comprising rail means adapted to be received in the armpit, thereby to support a user and transfer body weight to the frame, and so disposed and arranged that the point of load transfer in the kinetics of the body is disposed substantially adjacent to the said center of curvature, the frame having a central axis, the rail means being pivotally mounted to the frame and rotatable around the central axis.

18. A device according to claim 17 in which the spacing of said load transfer means from the arcuate edge is adjustable.

19. A device according to claim 17 in which hand-hold means is provided on said frame between the load transfer means and the arcuate edge.

20. A device according to claim 19 in which the device has an upright central axis, and in which the load transfer means is pivotally mounted to the frame so as to be rotatable around said axis.

21. A device according to claim 20 in which the spacing of said load transfer means from the arcuate edge is adjustable.

22. A device according to claim 17 in which shock absorbing means is incorporated in the rail means.

23. A device according to claim 17 in which the arcuate edge is circularly arcuate.

24. A device according to claim 17 in which the radius of curvature of the arcuate edge decreases in the forward direction.

25. An ambulation assistance device comprising: a frame including an arcuate edge for contacting the ground, said arcuate edge having a center of curvature; load transfer means on said frame for transferring weight to the frame, and so disposed and arranged that the point of load transfer in the kinetics of the body is disposed substantially adjacent to the said center of curvature; and support means pivotally attached to said frame at the point of load transfer thereto, said support means being swingable in the plane of forward ambulation, said support means being adapted swingingly to support a user of the device.

26. A device according to claim 25 in which a pair of said devices is provided, said support means being attached to each of them and including a seat disposed between them.

27. A device according to claim 26 in which the arcuate edge is circularly arcuate.

28. A device according to claim 26 in which the radius of curvature of the arcuate edge decreases in the forward direction.

29. An ambulation assistance device comprising: a frame including an arcuate edge for contacting the ground, said arcuate edge having a center of curvature; load transfer means on said frame engageable to or by the body for transferring body weight to the frame, and so disposed and arranged that the point of load transfer in the kinetics of the body is disposed substantially adjacent to the said center of curvature; a handle to adapt the device for usage as a cane and serve as load transfer means; and a flat region formed medially in the arcuate edge.

30. A device according to claim 29 in which the arcuate edge is formed by two laterally spaced-apart curved members.

* * * * *